United States Patent
Campbell et al.

(10) Patent No.: US 9,889,027 B2
(45) Date of Patent: Feb. 13, 2018

(54) STENT DELIVERY SYSTEM

(71) Applicant: Cook Medical Technologies LLC, Bloomington, IN (US)

(72) Inventors: Triona Campbell, Ballina (IE); Colm McElligott, Limerick (IE); Melissa Anenden, Queensland (AU); Gerard Treacy, Limerick (IE)

(73) Assignee: Cook Medical Technologies LLC, Bloomington, IN (US)

( * ) Notice: Subject to any disclaimer, the term of this patent is extended or adjusted under 35 U.S.C. 154(b) by 145 days.

(21) Appl. No.: 14/836,405

(22) Filed: Aug. 26, 2015

(65) Prior Publication Data
US 2017/0056221 A1    Mar. 2, 2017

(51) Int. Cl.
*A61F 2/06* (2013.01)
*A61F 2/95* (2013.01)
(Continued)

(52) U.S. Cl.
CPC ............ *A61F 2/95* (2013.01); *A61F 2/90* (2013.01); *A61F 2002/9505* (2013.01); *A61F 2002/9511* (2013.01); *A61F 2002/9665* (2013.01)

(58) Field of Classification Search
CPC ...... A61F 2002/9528; A61F 2002/9665; A61F 2002/9505; A61F 2002/9511;
(Continued)

(56) References Cited

U.S. PATENT DOCUMENTS 5,474,563 A * 12/1995 Myler .................. A61F 2/91
                                                        606/108
2008/0140178 A1    6/2008 Rasmussen et al.
(Continued)

FOREIGN PATENT DOCUMENTS

WO    WO 2008/098255 A2    8/2008
WO    WO 2009/102435 A1    8/2009
(Continued)

OTHER PUBLICATIONS

European Search Report for related application No. 16185787.5-1651 dated Nov. 8, 2016.

*Primary Examiner* — Jonathan Miles
*Assistant Examiner* — Majid Jamialahmadi
(74) *Attorney, Agent, or Firm* — Brinks Gilson & Lione (57) ABSTRACT

A stent delivery system is provided with an inner elongate shaft having a proximal portion and a distal portion and an outer elongate shaft having a lumen extending at least partially therethrough, wherein the proximal portion of the inner elongate shaft is at least partially movably disposed within the lumen. The system also includes a stent positionable about the inner elongate shaft having collapsed and expanded configurations. The system includes a proximal restraining member removably engaged with the outer elongate shaft and attached the stent, and a distal restraining member removably engaged with the inner elongate shaft and attached to the stent. The system also has a proximal biasing member operatively engaged with a distal portion of the outer elongate shaft, a distal biasing member operatively engaged with the distal portion of the inner elongate shaft, and an outer tube with a lumen movably disposed over the inner elongate shaft.

20 Claims, 8 Drawing Sheets (51) Int. Cl.
*A61F 2/90* (2013.01)
*A61F 2/966* (2013.01)

(58) Field of Classification Search
CPC .... A61F 2002/9522; A61F 2/966; A61F 2/95; A61F 2/954
USPC ............... 623/1.11, 1.12, 2.11; 606/108, 200
See application file for complete search history.

(56) References Cited

U.S. PATENT DOCUMENTS

| 2009/0099640 | A1 | 4/2009 | Weng |
| 2011/0077731 | A1* | 3/2011 | Lee .................... A61F 2/958 623/1.11 |

FOREIGN PATENT DOCUMENTS

| WO | WO 2010/040009 A1 | 4/2010 |
| WO | WO 2012/068175 A2 | 5/2012 |
| WO | WO 2012/068175 A3 | 5/2012 |
| WO | WO 2012/099731 A1 | 7/2012 |
| WO | WO 2013/003170 A1 | 1/2013 |
| WO | WO 2013/012493 A1 | 1/2013 |
| WO | WO 2013/055729 A1 | 4/2013 |

\* cited by examiner

STENT DELIVERY SYSTEM

TECHNICAL FIELD

This invention relates to a medical device and, in particular to a device for delivering and deploying a self-expanding stent and a method of delivering and deploying the stent into a body lumen.

BACKGROUND

Self-expanding stents are medical devices used to treat diseased areas of a variety of body lumens, including, but not limited to: veins, esophagi, bile ducts, colons, and ureters. Generally, self-expanding stents are used to support a weak point in the body lumen or to bypass it completely. A self-expanding stent is a tubular structure with at least one lumen that runs through it. Self-expanding stents are often made of a wire or mesh material that can elastically contract and expand.

A self-expanding stent is typically introduced into the body using a delivery device that includes an outer sheath coaxially disposed and slidable over an inner catheter. The stent is disposed at the distal end of the device between the inner catheter and the outer sheath and held in a compressed position by the outer sheath. The inner catheter and the outer sheath move coaxially with respect to each other. The stent may be deployed by proximally pulling the outer sheath relative to the inner catheter until the stent is exposed. The self-expanding stent then expands from the stent distal end to the stent proximal end as the sheath is proximally withdrawn.

Several problems may occur with the sheathed delivery device described above. Sheath release delivery devices are difficult to reposition or remove and slow to operate. Often, the stent is first partially deployed to determine whether the stent is properly positioned within the body lumen. Partial deployment is achieved by withdrawing the outer sheath so that only a portion of the self-expanding stent is exposed. The stent may then be reconstrained by pushing the outer sheath back over the entire length of the stent, thus allowing the stent to be repositioned or removed. However, once the stent is fully deployed, i.e. radially expanded, the sheath cannot reconstrain the stent. For example, utilizing a conventional outer sheath/inner catheter delivery device may cause the physician to inadvertently use excessive force and pull back the outer sheath too far, thereby prematurely deploying the stent in an incorrect position within a body lumen. At this step in the procedure, repositioning of the stent becomes difficult, if not impossible, because the stent has already radially self-expanded in the body lumen. Additionally, retraction of the outer sheath with controlled movement may not be achieved because the physician is manually retracting the outer sheath which may lead to uneven or inadvertent movement of the outer sheath that can lead to improper positioning of the stent.

Additionally, in a typical sheath release device where the outer sheath is proximally withdrawn, the first portion of the self-expanding stent to make contact with the body vessel is the most distal portion of the stent. This type of release may cause difficulty in accurately placing the proximal portion of the stent because the distal end of the stent is positioned first while the proximal portion of the stent is still covered by the outer sheath. Accurate placement of the proximal portion of the stent and/or the stent body may be important in certain applications such as to prevent stent migration. Additionally, conventional sheathed stent delivery systems may cause problems where direct visualization of the stent is required. For example, in endoscopically placed stents, the sheath tends to prevent or obscure the location of the stent, making accurate placement of the stent more difficult.

Further potential drawbacks for the conventional sheathed stent delivery system involve the stent placement within the system prior to use within a patient. Loading and anchoring of a conventional sheathed stent delivery device is an involved process that may require preloading the stent into the device so that the stent remains compressed within the sheath during shipment and storage prior to use in the patient. Extended compression of the stent may lead to an alteration in the stent mechanical properties.

Conventional sheathed stent delivery devices also require a high force to overcome the friction between the stent and the sheath that may also be a problem for proper stent placement within the patient. The introducer must be mechanically strong enough to overcome the frictional forces between the sheath and the stent to avoid undesirable frictional consequences such as stretching of the introducer catchers and hysterics in the movement of the stent. The sheathed stent delivery device also requires more space within an endoscope compared to a sheathless device and also adds additional expense to the delivery system.

Accordingly, in view of the drawbacks of current technology, there is a desire for a delivery system that can increase the control, accuracy and ease of placement of a stent during deployment of the stent within a lumen within a patient. The delivery system would ideally reduce the risk of malfunction while providing for a smoother, more accurate and quicker deployment of the entire stent. The delivery system also would provide the ability to recollapse, recapture, reposition and/or remove the stent after expansion of the stent.

BRIEF SUMMARY

In one aspect of the present invention, a stent delivery system is provided. The stent delivery system comprises an inner elongate shaft comprising a proximal portion and a distal portion and an outer elongate shaft comprising a lumen extending at least partially therethrough, wherein the proximal portion of the inner elongate shaft is at least partially movably disposed within the lumen. The system further comprises a stent positionable about the inner elongate shaft having a collapsed configuration and an expanded configuration. The system also comprises at least one proximal restraining member removably engaged with the outer elongate shaft, wherein the at least one proximal restraining member is also attached to the stent and at least one distal restraining member removably engaged with the inner elongate shaft, wherein the at least one distal restraining member is also attached to the stent. The system further comprises a proximal biasing member operatively engaged with at least a distal portion of the outer elongate shaft, the proximal biasing member configured to prevent unintentional disengagement of the proximal restraining member from the outer elongate shaft, and a distal biasing member operatively engaged with the distal portion of the inner elongate shaft, the distal biasing member configured to prevent unintentional disengagement of the distal restraining member from the inner elongate shaft. Additionally, the system comprises an outer tube comprising a lumen extending at least partially therethrough, wherein the distal portion of the inner elongate shaft is at least partially movably disposed within the lumen of the outer tube, wherein the outer tube is disposed between the proximal biasing member and the distal biasing member.

Additionally, movement of the inner elongate shaft relative to the outer elongate shaft in a first direction releases tension to the proximal and distal restraining members to move the stent to the expanded configuration.

The stent delivery system may further comprise a first position and a second position, wherein the inner elongate shaft is moved proximally with respect to the outer elongate shaft to move the stent delivery system from the first position to the second position and the stent is in the expanded configuration in the second position and the stent is in the collapsed configuration in the first position. The stent delivery system may also further comprise a third position, wherein the inner elongate shaft is moved proximally with respect to the outer elongate shaft to move the stent delivery system from the second position to the third position, wherein in the third position the at least one proximal restraining member is released from the outer elongate shaft and the at least one distal restraining member is released from the inner elongate shaft, thus releasing the stent from about the inner elongate shaft. In another embodiment, a proximal portion of the proximal biasing member is fixedly secured to the outer elongate shaft and a distal portion of the distal biasing member is fixedly secured to the inner elongate shaft, wherein when the stent delivery system is moved from the second position to the third position the outer tube pushes a distal portion of the proximal biasing member in a proximal direction and a proximal portion of the distal biasing member in a distal direction. The stent delivery system may additionally comprise at least one proximal restraining member removably engaged with the outer elongate shaft by a proximal hook fixedly attached to the outer elongate shaft, and the at least one distal restraining member removably engaged with the inner elongate shaft by a distal hook fixedly attached to the inner elongate shaft, wherein the distal hook is attached to the inner elongate shaft at a point distal to the proximal hook. Further, in the first and second position the at least one proximal restraining member is engaged with the proximal hook and the at least one distal restraining member is engaged with the distal hook, wherein in the third position the at least one proximal restraining member is released from the proximal hook and the at least one distal restraining member is released from the distal hook.

The stent delivery system may also comprise a proximal end stop fixedly attached to a distal portion of the outer elongate shaft and a distal end stop fixedly attached to the distal portion of the inner elongate shaft. It may also comprise a proximal pusher sleeve slidably disposed about the proximal portion of the inner elongate shaft and a distal portion of the outer elongate shaft and disposed between the proximal end stop and the outer tube, and a distal pusher sleeve slidably disposed about the distal portion of the inner elongate shaft and disposed between the distal end stop and the outer tube. Further, the distal biasing member is disposed between the distal end stop and the distal pusher sleeve and the proximal biasing member is disposed between the proximal end stop and the proximal pusher sleeve and when the stent delivery system is moved from the second position to the third position the outer tube pushes the proximal pusher sleeve and the proximal biasing member in a proximal direction and the distal pusher sleeve and the distal biasing member in a distal direction. In another embodiment, the proximal restraining member may be removably engaged with the outer elongate shaft by a proximal hook fixedly attached to the outer elongate shaft and the distal restraining member may be removably engaged with the inner elongate shaft by a distal hook fixedly attached to the inner elongate shaft, wherein the distal hook is attached to the inner elongate shaft at a point distal to the proximal hook. Further, in the first and second position the at least one proximal restraining member may be engaged with the proximal hook and the at least one distal restraining member may be engaged with the distal hook, wherein in the third position the at least one proximal restraining member is released from the proximal hook and the at least one distal restraining member is released from the distal hook.

In another aspect of the invention, a method of delivering a stent is provided. The method comprises inserting a distal portion of a stent delivery system into a body lumen of a patient. The stent delivery system comprises an inner elongate shaft comprising a proximal portion and a distal portion, an outer elongate shaft comprising a lumen extending at least partially therethrough, wherein the proximal portion of the inner elongate shaft is at least partially movably disposed within the lumen, a stent positionable about the inner elongate shaft, the stent having a collapsed configuration and an expanded configuration, at least one proximal restraining member removably engaged with the outer elongate shaft, wherein the at least one proximal restraining member is also attached to the stent, at least one distal restraining member removably engaged with the inner elongate shaft, wherein the at least one distal restraining member is also attached to the stent, a proximal biasing member operatively engaged with at least a distal portion of the outer elongate shaft, the proximal biasing member configured to prevent unintentional disengagement of the proximal restraining member from the outer elongate shaft, a distal biasing member operatively engaged with the distal portion of the inner elongate shaft, the distal biasing member configured to prevent unintentional disengagement of the distal restraining member from the inner elongate shaft, and an outer tube comprising a lumen extending at least partially therethrough, wherein the distal portion of the inner elongate shaft is at least partially movably disposed within the lumen of the outer tube, wherein the outer tube is disposed between the proximal biasing member and the distal biasing member. The method further comprises maintaining the stent in the collapsed configuration with the inner and outer elongate shafts in a first position and tension applied to the at least one proximal and at least one distal restraining members for delivery of the stent to an implant site, and positioning the stent at the implant site. The method also comprises expanding the stent to the expanded configuration by moving the inner and outer elongate shafts relative to each other to a second position, thereby releasing tension on the proximal and distal restraining members so that the stent moves to the expanded configuration. The method may also comprise returning the inner and elongate shafts to the first position to move the stent from the expanded configuration to the collapsed configuration. In another contemplation, the method may further comprise releasing the stent from about the outer elongate shaft at the implant site by moving the inner and outer elongate shafts relative to each other to a third position so that the proximal restraining member is released from the outer elongate shaft and the distal restraining members is released from the inner elongate shaft.

DETAILED DESCRIPTION

The invention is described with reference to the drawings in which like elements are referred to by like numerals. The relationship and functioning of the various elements of this invention are better understood by the following detailed description. However, the embodiments of this invention as described below are by way of example only, and the invention is not limited to the embodiments illustrated in the drawings. It should also be understood that the drawings are not to scale and in certain instances details have been omitted, which are not necessary for an understanding of the present invention, such as conventional details of fabrication and assembly.

As used in the specification, the terms proximal and distal should be understood as being in the terms of a physician using the delivery system. Hence the term distal means the portion of the delivery system which is farthest from the physician and the term proximal means the portion of the delivery system which is nearest to the physician.

Figure 1:
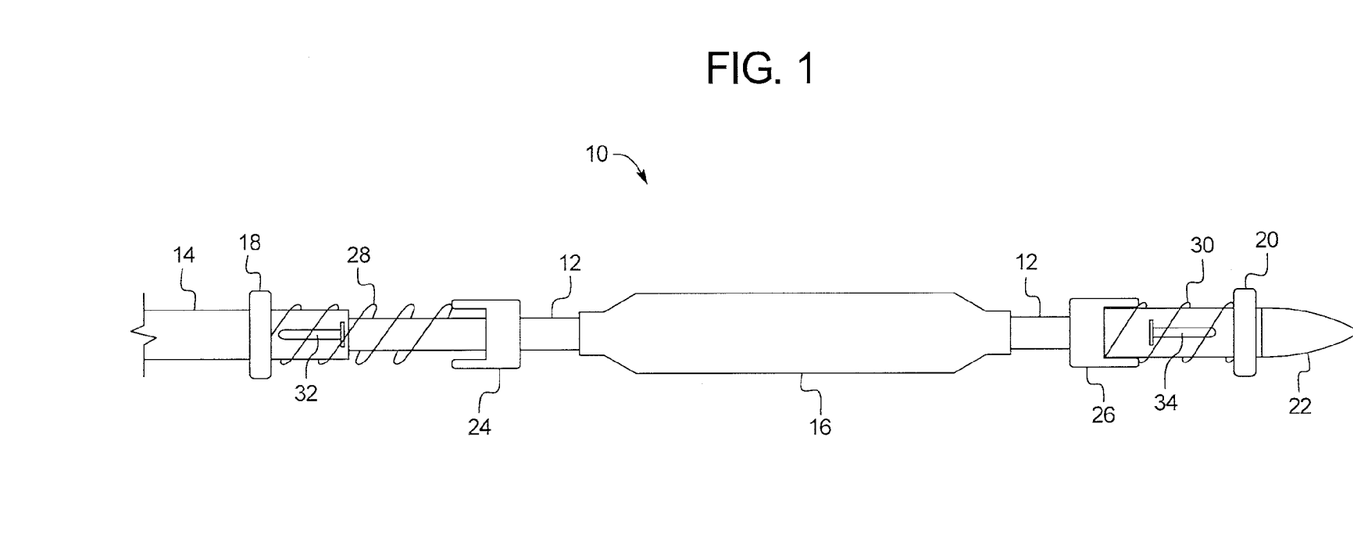
FIG. 1 is a side view of distal portion a stent delivery system in a first position according to an embodiment of the present invention.

FIG. 1 illustrates a distal end of a stent delivery system 10 in accordance with embodiments of the present invention. The stent delivery system 10 may include an inner cannula 12 and an outer cannula 14. The outer cannula 14 (or outer elongate shaft) may be an elongate shaft with a lumen within which a portion of the inner cannula 12 (or inner elongate shaft) is movably disposed. The inner cannula 12 may optionally have a lumen for a wire guide. An outer tube 16 may be movably disposed over a distal portion of the inner cannula 12. A proximal end stop 18 may be fixedly secured to a distal portion of the outer cannula 14. A distal end stop 20 may be fixedly secured to the distal end of the inner cannula 12 or a tip 22 of the stent delivery system 10. A proximal pusher sleeve 24 may be positioned between the outer tube 16 and the proximal end stop 18. The proximal pusher sleeve 24 may be freely slidable over both the inner cannula 12 and outer cannula 14. A distal pusher sleeve 26 may be positioned between the outer tube 16 and the distal end stop 20. The distal pusher sleeve 26 may be freely slidable over the inner cannula 12. Positioned between the proximal end stop 18 and the proximal pusher sleeve 24 is a proximal spring 28. The one end of the proximal spring 28 may be fixedly secured to the proximal end stop 18, while the other end may be optionally secured to the proximal pusher sleeve 24. A distal spring 30 may be positioned between the distal end stop 20 and the distal pusher sleeve 26. One end of the distal spring 30 may be fixedly secured to the distal end stop 20, while the other end may be optionally secured to the distal pusher sleeve 26. While in this embodiment, springs are used, any other biasing member may be used in place of the proximal and distal springs 28, 30. A proximal hook 32 may be attached to the outer cannula 14 at a point distal the proximal end stop 18, while a distal hook 34 may be attached to the inner cannula 12 at a point proximal the distal end stop 20. A stent (not shown) may be loaded over the inner cannula 12, outer cannula 14, and outer tube 16. The stent may be attached to the stent delivery system 10 at the proximal and distal hooks 32, 34.

Figure 2:
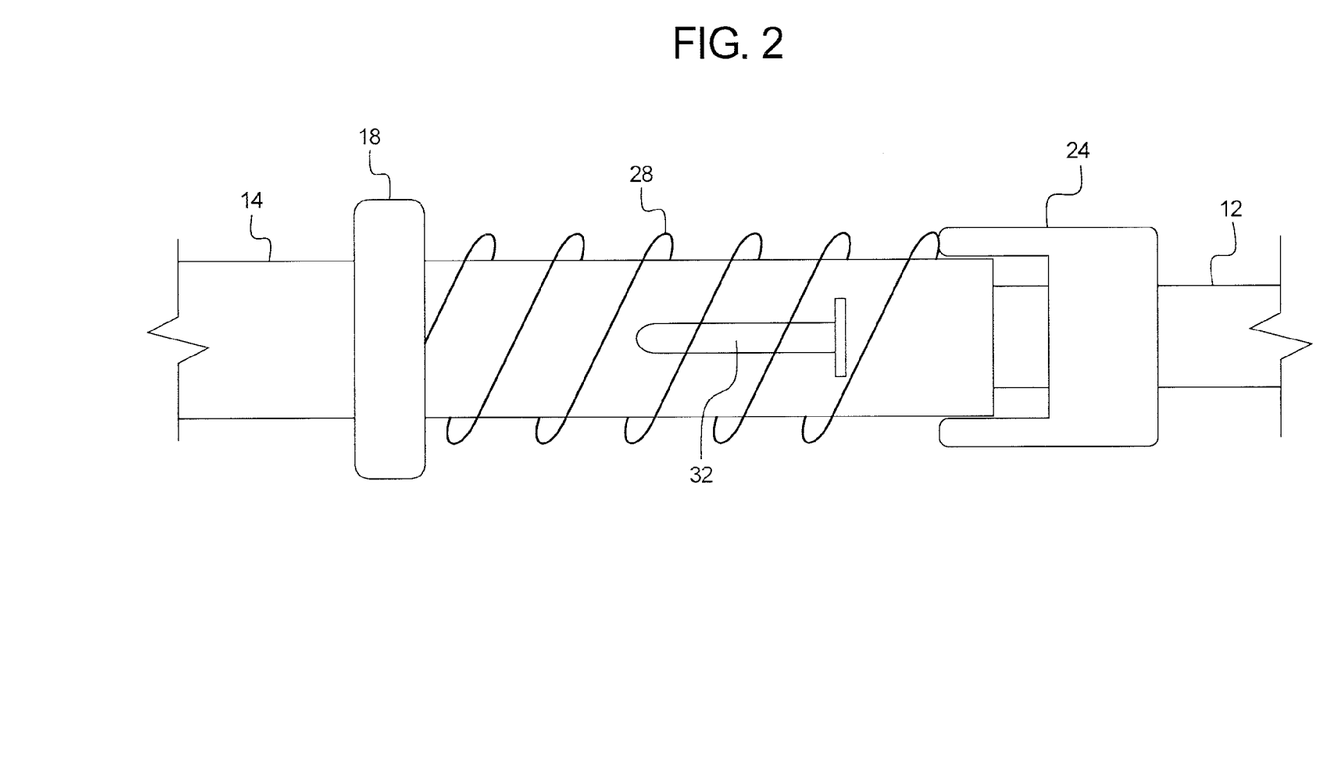
FIG. 2 is a detailed view of the hook system of the stent delivery system in a first position.
Figure 3:
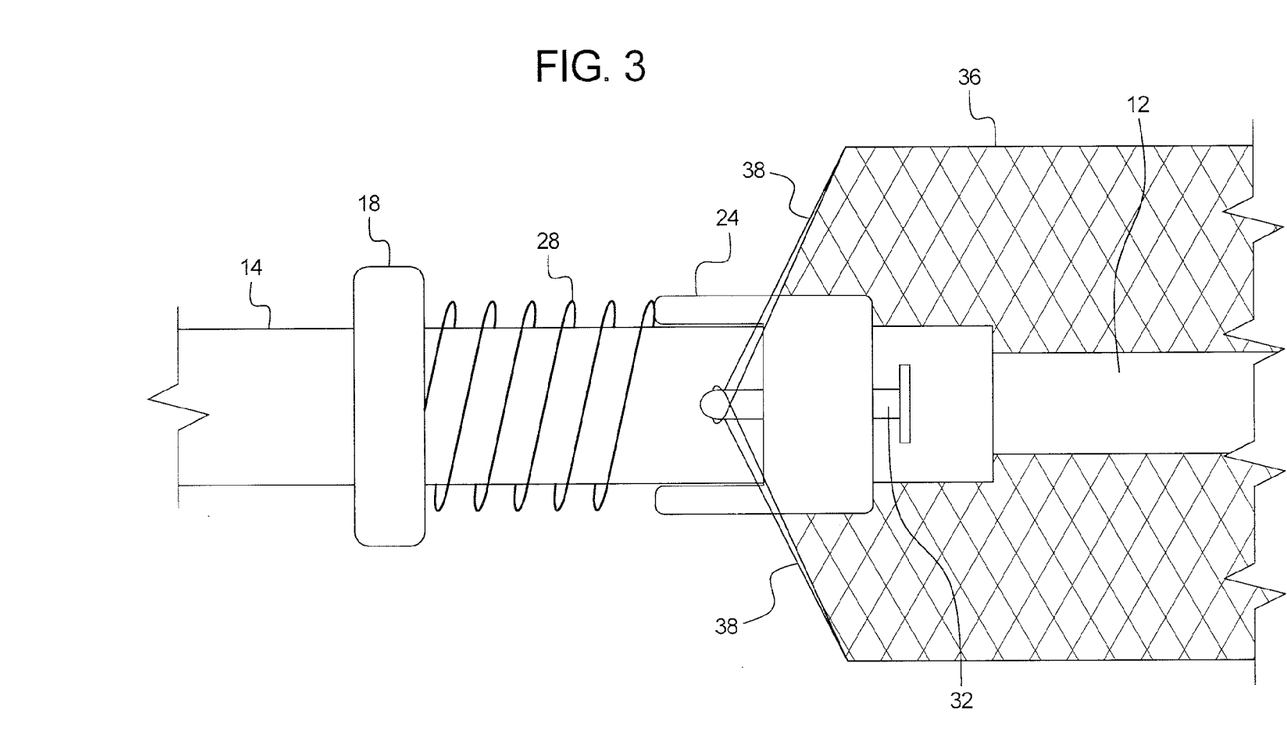
FIG. 3 is a detailed view of the hook system of the stent delivery system in a second position.
Figure 4:
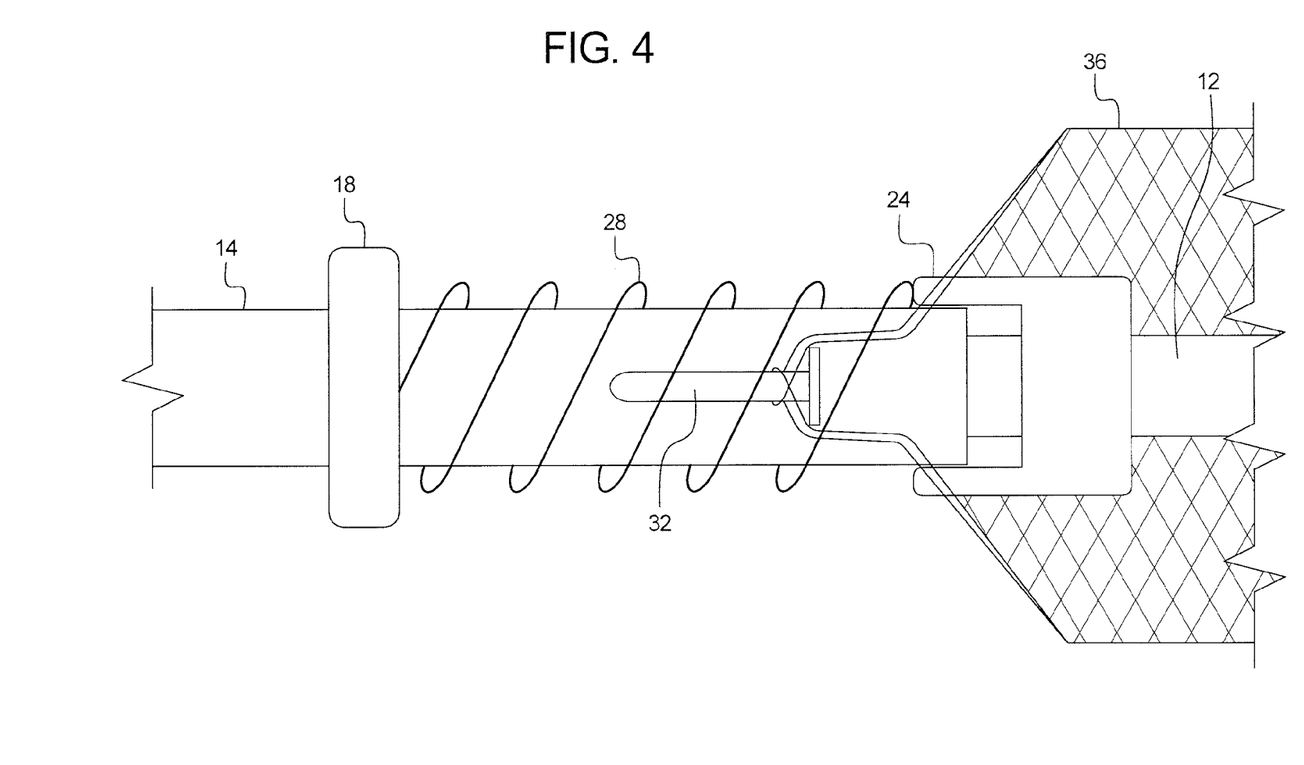
FIG. 4 is a detailed view of the hook system of the stent delivery system in a first position.

FIGS. 2, 3, and 4 show detailed views of the stent 36 and how it may be attached to the stent delivery system 10. As shown in FIG. 2, when the stent delivery system 10 is in its natural state without any external forces applied, the proximal spring 28 covers the proximal hook 32. To expose the proximal hook 32, the proximal pusher sleeve 24 is advanced proximally, thus contracting the proximal spring 28 until the proximal hook 32 is exposed. Once the proximal hook 32 is exposed, as shown in FIG. 3, one or multiple suture loops 38, or restraining members, are looped around the proximal hook 32 at one end, and attached to the stent 36 at the other end. The proximal pusher sleeve 24 is then released and the proximal spring 28 pushes the proximal pusher sleeve 24 distally to its original, natural position. The proximal spring 28 covers a portion of the suture loops 38 while applying a distal force to them, thus securing them and, by extension, the stent 36 to the proximal hook 32 and the stent delivery system 10. The same process is repeated at the distal end of the stent delivery system 10, thus securing the distal end of the stent 36 to the distal hook 34 with additional suture loops 38. While suture loops 38 are used in the present embodiment, any other similar restraining members may be used instead.

Figure 5:
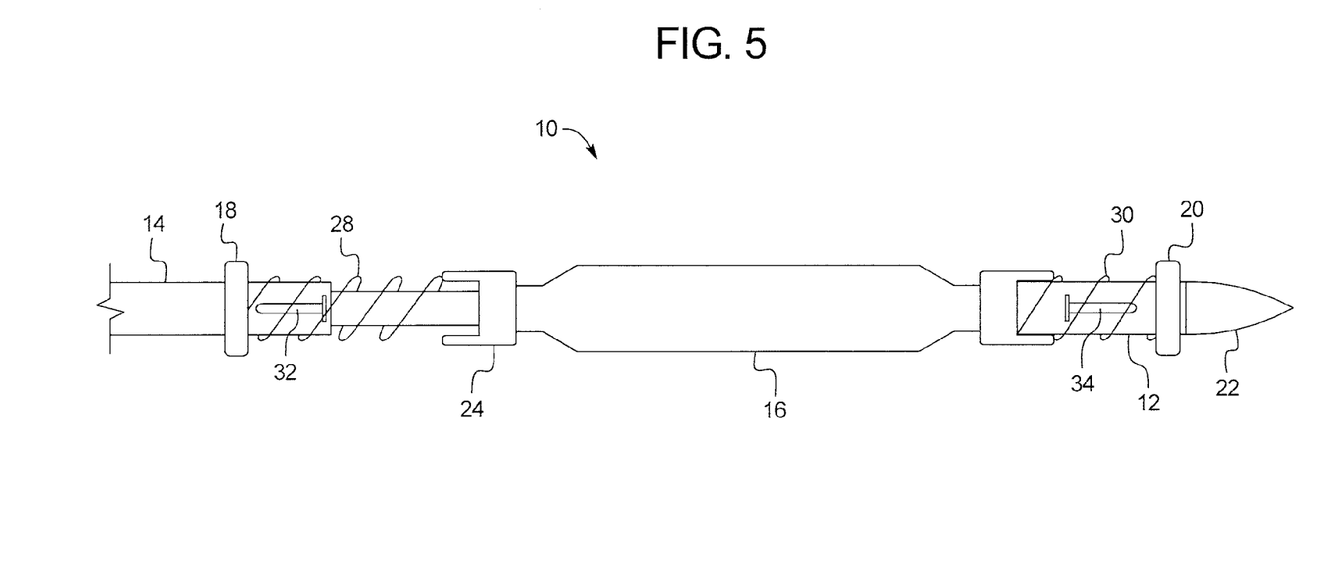
FIG. 5 is a side view of distal portion a stent delivery system in a second position.

FIG. 1 shows the stent delivery system 10 in a first position; however, the stent delivery system 10 may also have at least a second position (FIG. 5). The operator may alternate between the two positions by moving the inner cannula 12 relative to the outer cannula 14. To move the stent delivery system 10 from the first position to the second position, the inner cannula 12 is moved proximally relative to the outer cannula 14. The stent 36 (not shown in FIGS. 1 and 5) may be movable between a collapsed and an expanded configuration. In the collapsed configuration, the stent 36 is longitudinally extended along the stent delivery system 10, which causes the stent 36 to correspondingly collapse in an axial direction. In the expanded configuration, the stent 36 is longitudinally contracted along the stent delivery system 10, which causes the stent 36 to correspondingly expand axially. When the stent 36 is attached to the stent delivery system 10, the first position of the stent delivery system 10 corresponds to the collapsed configuration of the stent 36, while the second position of the stent delivery system 10 corresponds to the expanded configuration of the stent 36. The proximal hook 32 is located at a fixed position on the outer cannula 14, while the distal hook 34 is located at a fixed position on the inner cannula 12. Thus, as the inner cannula 12 and outer cannula 14 are moved longitudinally with respect to each other, the distance between the distal and proximal hooks 32, 34 either increases or decreases. Since one end of the stent 36 is attached to the distal hook 34 and the other end is attached to the proximal hook 32, as the inner cannula 12 and outer cannula 14 are moved with respect to each other, a tension is applied or released to the stent 36 through the suture loops 38, thus causing the stent 36 to correspondingly collapse or expand. When the stent delivery system 10 is in the first position, the proximal hook 32 and distal hook 34 are at distance that causes a tension to be applied to the stent 36, thus maintaining the stent 36 in the collapsed configuration. As the stent delivery system 10 is moved to the second position, the distance between the proximal and distal hooks 32, 34 decreases, therefore releasing the tension on the stent 36 and thus allowing the stent 36 to longitudinally contract and axially expand into the expanded configuration.

Figure 6:
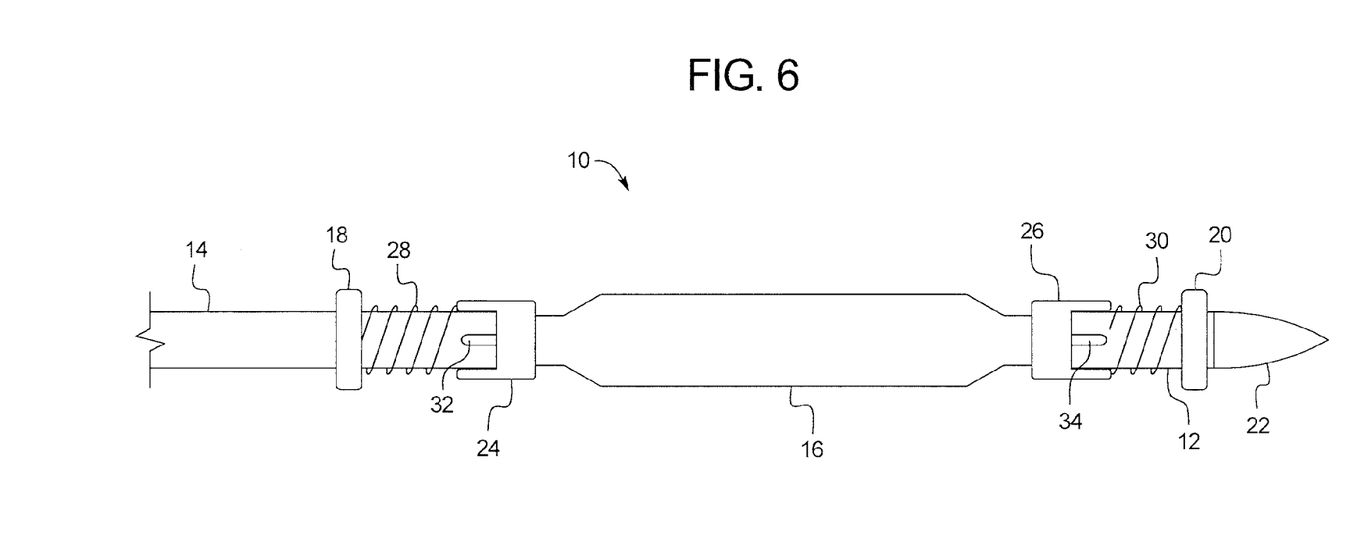
FIG. 6 is a side view of distal portion a stent delivery system in a third position.
Figure 7:
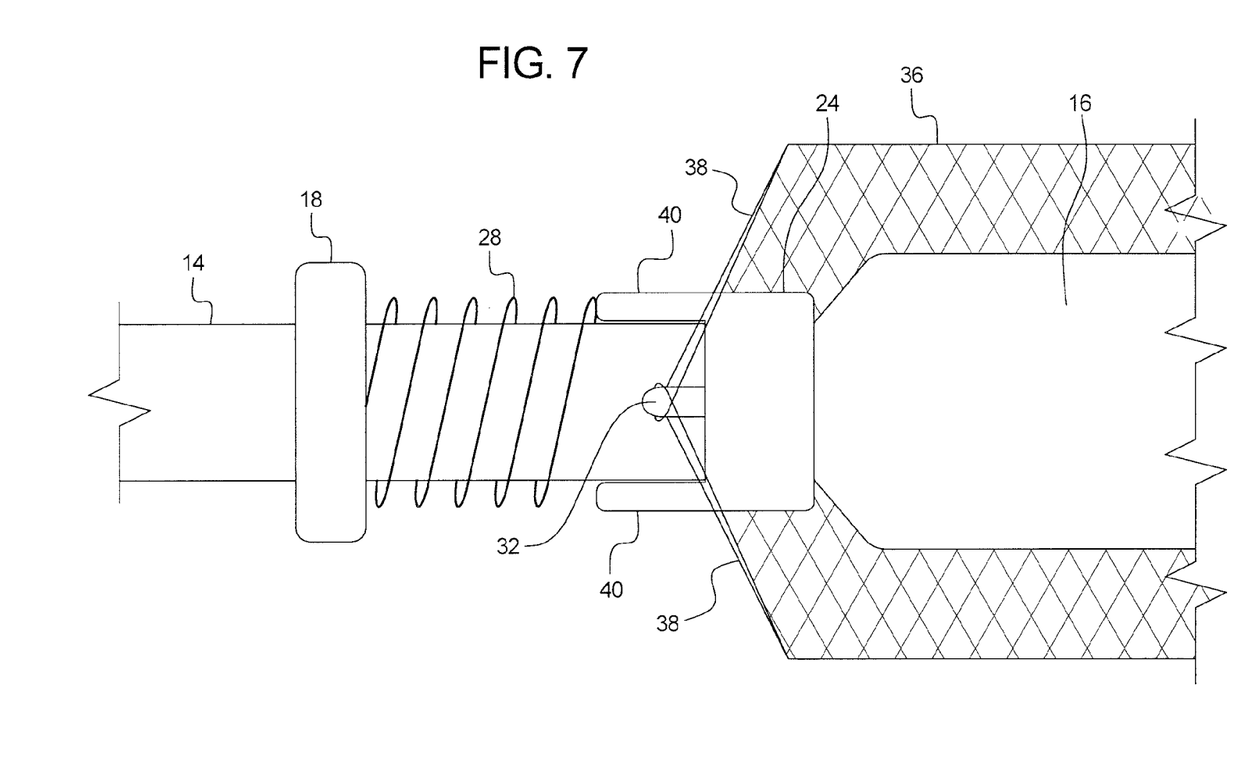
FIG. 7 is a detailed view of the hook system of the stent delivery system in a third position.

As shown in FIGS. 6 and 7, the stent delivery system 10 may also have a third position. To move the stent delivery system from the second position to the third position, the inner cannula 12 is again moved proximally relative to the outer cannula 14. As the inner cannula 12 continues to be moved in a proximal direction, an increasing amount of the distal portion of the inner cannula 12 will be pulled into the lumen of the outer cannula 14. Because of this movement, eventually one end of the outer tube 16 will contact the proximal pusher sleeve 24 and the other end of the outer tube 16 will contact the distal pusher sleeve 26. At this point, any further proximal movement of the inner cannula 12 will cause the outer tube 16 to force the proximal pusher sleeve 24 in a proximal direction against the proximal spring 28 and the distal pusher sleeve 26 in a distal direction against the distal spring 30. As both pusher sleeves 24, 26 are forced in their respective directions, their respective springs 28, 30 will contract. As shown in detail in FIG. 7, (and as is similarly happening on the distal end of the stent delivery system 10) once the outer tube 16, due to the motion of the inner cannula 12, pushes the proximal pusher sleeve 24 proximally to the third position, the proximal hook 32 is exposed and the proximal pusher sleeve 24 pushes the suture loops 38 off the proximal hook 32, thus releasing the suture loops 38, and by extension the stent 36, from about the stent delivery system 10. Once the stent 36 is released from about the stent delivery system 10, the stent 36 is fully deployed in the target body lumen. Because the operator must apply a deliberate directional force to the stent delivery system to deploy the stent 36, accidental or premature deployment of the stent 36 is unlikely. For example, the chance of accidental deployment while the stent 36 is being delivered to the diseased site is lessened.

In this embodiment, both pusher sleeves 24, 26 have a U-shaped design, with prongs 40. The prongs 40 of the pusher sleeves 24, 26 are designed to contact and push the springs 28, 30, thus leaving a gap between the prongs 40 where the hooks 32, 34 can be exposed. Thus, when the suture loops 38 are pushed off the hooks 32, 34 by the pusher sleeves 24, 26, there is a gap that allows them to freely release from the stent delivery system 10 without getting caught on the springs 28, 30. However, a design omitting the pusher sleeves 24, 26 altogether is possible. By omitting the pusher sleeves 24, 26, the outer tube 16 may directly contact the springs 28, 30 and push them in their respective directions. The outer tube 16 may also include integral prongs 40 on each end, thus eliminating the need for the pusher sleeves 24, 26 altogether. Additionally, while hooks 32, 34 are used to secure the suture loops 38 to the stent delivery system 10, any structure or method capable of removably securing the suture loops 38 to the stent delivery system 10 may be used. Also, while single hooks 32, 34 are used on each end of the stent delivery system 10, multiple hooks can be used at each end. For example, the proximal hook 32 may be replaced with two or more hooks with individual suture loops 38 attached to each hook and the stent 38.

The stent 36 is ideally a self-expandable woven or braided stent, thus allowing the stent 36 to automatically expand once freed from about the stent delivery system 10. By way of non-limiting example, the stent 36 may be formed as a woven or braided mesh formed from a metal or polymer or a laser cut pattern formed in a metal stent. The stent delivery system 10 uses the axial elongation of compressed woven, braided, or laser cut stents, normally considered a disadvantage, as an advantage to eliminate the need for a delivery sheath. The stent may also be formed from a bioabsorbable material. One example of a woven stent is the EVOLUTION® stent (Wilson-Cook Medical, Inc.).

The suture loops 38 may each be attached to the stent 36 at single points, or they may be woven through the respective ends of the stent 36. Thus, when tension is applied to the suture loops 38, the ends of the stent 36 will radially close in addition the stent 36 elongating and collapsing, thus allowing a more uniformly collapsed profile.

Figure 8:
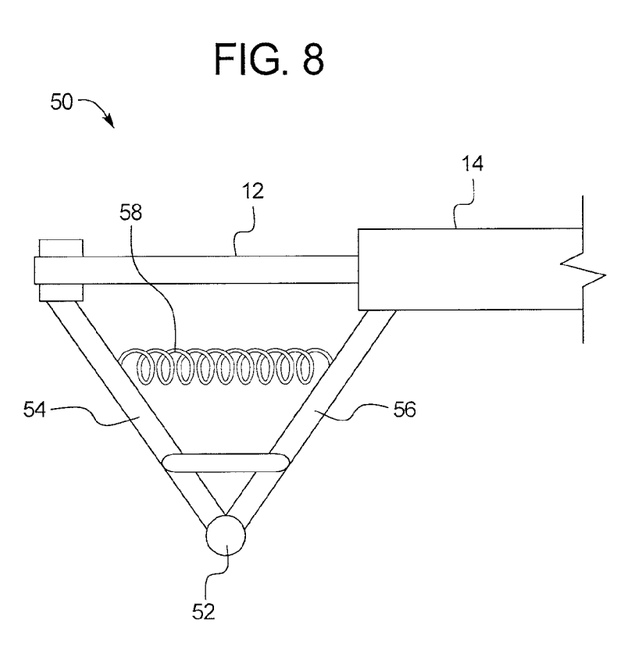
FIG. 8 is a detailed view of a handle of the stent delivery system.

As shown in FIG. 8, a handle 50 attached to the proximal end of the stent delivery system 10 may be used to assist the operator in manipulating the inner cannula 12 relative to the outer cannula 14. A hinge 52 allows the left arm 54 and right arm 56 of the handle 50 to pivot with respect to each other, thus allowing the outer cannula 14 and inner cannula 12 to move correspondingly. Thus, the operator may use the handle 50 to easily move the stent delivery system 10 between the first, second, and third positions. The handle 50 may also include a spring 58 or other biasing member to bias the handle 50 in a certain position. In one embodiment, the spring 58 may bias the stent delivery system 10 towards the first position, thus requiring deliberate manipulation of the handle by the physician to move the stent delivery system 10 into the second and third positions. Alternatively, the spring 58 may bias the stent delivery system 10 towards the second, or even third, positions. In some embodiments, a lock 60 may be used to releasably lock the handle 50 in any longitudinal position, such as the first, second, or third positions. Alternatively, separate handles may be used for the inner cannula 12 and the outer cannula 14, with a lock 60 between them. Also alternatively, handles may be omitted altogether and the operator may directly manipulate the inner and outer cannulas 12, 14.

The design of the stent delivery system 10 may be altered to achieve various desirable characteristics. For example, the stent delivery system 10 may be designed such that the outer tube 16 is in contact with the proximal and distal pusher sleeves 24, 26 when the stent deployment system 10 is in the first position. Thus, the proximal and distal springs 28, 30 will apply a resistive force to any attempted movement of the stent delivery system 10 to the second position, and further to the third position. Therefore the default, natural state of the stent deployment system 10 will be in the first position, which allows easier maneuverability within a body lumen without having to ensure the stent 36 remains collapsed. Similarly, the stent delivery system 10 may be designed such that the outer tube 16 initially contacts the proximal and distal pusher sleeves 24, 26 when the stent delivery system 10 is in the second position. Thus, the stent delivery system 10 is freely movable between the first and second positions; but when moving the stent delivery system 10 from the second position to the third position, the proximal and distal springs 28, 30 will provide a resistive force. This resistive force may provide a cue to the operator that any further movement towards the third position may result in premature or accidental deployment of the stent 36. Thus, the operator may freely move the stent delivery system 10 between the first and second positions without fear of accidental deployment, and will have to apply a greater, deliberate force to move the stent delivery system 10 to the third position and deploy the stent 36.

In accordance with the alternative design choices discussed above, the proximal and distal springs 28, 30 may also be altered to achieve various desirable results. For example, it is often desirable to control which portion of the stent 36 is deployed first. To achieve this controlled deployment, the distal spring 30 may be shorter in length than the proximal spring 28 or have a lower requisite force to compress the distal spring 30 a certain distance. Thus, when the outer tube 16 is pushing against and compressing both the proximal and distal springs 28, 30, the shorter length of the distal spring 30 or reduced requisite force to compress the distal spring 30 will cause the distal hook 34 to be exposed prior to exposure of the proximal hook 32, thus causing the distal end of the stent 36 to release from about the stent deployment system 10 first. Alternatively, the proximal spring 28 may be designed to allow the proximal end of the stent 36 to deploy first. As an alternative to changing the design of the springs 28, 30, the location of the proximal and distal hooks 32, 34 may be altered to achieve the same results.

While not necessary, the stent delivery system 10 may include a standard delivery sheath slidably positionable over a portion of the stent delivery system 10 to cover the stent 36. The optional delivery sheath may form a smooth outer surface to facilitate a smoother delivery of the stent 36 to the desired location. For example, the smooth outer surface may prevent damage to the walls of the body lumen or damage to the stent 36 while the stent delivery system 10 is being inserted into the body lumen. When present, the delivery sheath may provide some compressive force to the stent 36. Once the stent delivery system 10 is at the desired location, the delivery sheath may be removed by sliding the delivery sheath proximally with respect to the stent delivery system 10 until the delivery sheath has been withdrawn from the patient's body lumen. Once the delivery sheath is removed, the stent delivery system 10 may be used as previously described.

While the embodiment discussed above makes use of certain components to achieve the desired functionality of the stent delivery system 10, other components that perform the same functions may be used. For example, the proximal end stop 18 may be replaced with any structure capable of preventing the proximal end of the proximal spring 28 from sliding along the stent delivery system 10 in a proximal direction. Alternatively, the proximal end stop 18 may be removed entirely and the proximal spring 28 may be fixedly secured to the outer cannula 14. Similar substitutions may be made for the distal end stop 20.

In some embodiments, the suture loops 38 may remain attached to the stent 36 after the stent delivery system 10 is withdrawn. The suture loops 38 may be designed to be biodegradable. Additionally, while this embodiment utilizes suture loops 38 to secure the stent 36 to the stent delivery system 10, any type of mechanism that can releaseably hold the stent 36 in an expanded and collapsed configuration may be used. By way of non-limiting example, the suture loops 38 may be substituted with releasable bands, hooks, adhesives, wires, and the like.

The materials used to manufacture the components of the stent delivery systems described herein may be any materials known to one skilled in the art that are suitable for use in patients. By way of non-limiting example, the inner cannula, outer cannula and delivery sheath may be formed from polytetrafluoroethylene (PTFE) particularly when a low friction delivery sheath is desirable. Nylon and HDPE may also be used for clarity. Additional possible materials include, but are not limited to the following, polyethylene ether ketone (PEEK), fluorinated ethylene propylene (FEP), perfluoroalkoxy polymer resin (PFA), polyamide, polyurethane, high density or low density polyethylene, and nylon including multi-layer or single layer structures and the like and may also include reinforcement wires, braid wires, coils, coil springs and or filaments.

The stent may be formed from but is not limited to the following materials: Nickel titanium alloys, for example, nitinol, stainless steel, cobalt alloys and titanium alloys. The wires may be made from a metallic alloy such as stainless steel or nickel titanium. In some embodiments, the restraining members may be made from polymers having sufficient strength to hold the stent in the collapsed configuration. The restraining members may be single, multiple, braided or twisted. In some embodiments, the restraining members or segments thereof may be coated, for example with a coating such as PTFE. In some embodiments, the stent and/or the restraining members may be made from biodegradable materials. A number of bioabsorbable homopolymers, copolymers, or blends of bioabsorbable polymers are known in the medical arts. These include, but are not necessarily limited to, polyesters including poly-alpha hydroxy and poly-beta hydroxy polyesters, polycaprolactone, polyglycolic acid, polyether-esters, poly(p-dioxanone), polyoxaesters; polyphosphazenes; polyanhydrides; polycarbonates including polytrimethylene carbonate and poly(iminocarbonate); polyesteramides; polyurethanes; polyisocyanates; polyphosphazines; polyethers including polyglycols, polyorthoesters; epoxy polymers including polyethylene oxide; polysaccharides including cellulose, chitin, dextran, starch, hydroxyethyl starch, polygluconate, hyaluronic acid; polyamides including polyamino acids, polyester-amides, polyglutamic acid, polylysine, gelatin, fibrin, fibrinogen, casein, collagen.

Other suitable biocompatible materials may also be used for any of the components described herein.

Operation of the stent delivery system 10 of the present invention is described with reference to the stent delivery system 10 by way of non-limiting example. Alternative methods of operating the system may also be used. The stent delivery system 10 may be provided in a sterile packaging. The stent 36 may be provided in the expanded configuration or collapsed configuration within the packaging. For example, some stent materials may weaken or otherwise deform when stored in a collapsed configuration during shipping and storage. The stent 36 may be provided in the expanded configuration and be moved to the collapsed configuration to the first position prior to delivery into the patient.

The delivery system 10 may be delivered to the patient using an endoscope that may be positioned within the body lumen so the operator can view a proximal side of the diseased area to be treated with the stent 36. The operator inserts the stent delivery system 10 into the patient's body lumen with the stent 36 in the collapsed configuration. A wire guide may be inserted first to assist in navigating the endoscope to the diseased site and the system 10 is then delivered through the working channel of the endoscope over the wire guide to the diseased site. The inner cannula 12 may have a lumen that receives the wire guide, or the inner cannula may be a solid elongate shaft. Alternatively, the stent delivery system 10 may be inserted into the patient's lumen without the use of an endoscope, depending on the size and location of the lumen.

The collapsed stent 36 may be moved within the body lumen to correctly position the stent 36 at the diseased site. The stent delivery system 10 is moved to the second position and the stent 36 is correspondingly moved to the expanded configuration by proximal movement of the inner cannula 12 relative to the outer cannula 14. The position of the expanded stent 36 can be monitored through fluoroscopy or other methods well known in the art. If necessary, such as if the stent 36 is incorrectly positioned, the physician may return the stent delivery system 10 to the first position and thus the stent 36 to the collapsed configuration by moving the inner cannula 12 distally with respect to the outer cannula 14. The stent delivery system 10 may be moved from the first position to the second position, and thus the stent 36 from the collapsed configuration to the expanded configuration, as many times as needed.

Once proper position for the stent 16 is achieved within the patient's body lumen, the stent delivery system 10 may then be moved to the third position, therefore causing the stent 36 to release from about the stent delivery system 10 and fully expand in the body lumen. The delivery system 10 may then be withdrawn proximally from the patient.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A stent delivery system, comprising:
   an inner elongate shaft comprising a proximal portion and a distal portion;
   an outer elongate shaft comprising a lumen extending at least partially therethrough, wherein the proximal portion of the inner elongate shaft is at least partially movably disposed within the lumen;
   a stent positionable about the inner elongate shaft, the stent having a collapsed configuration and an expanded configuration;
   at least one proximal restraining member removably engaged with the outer elongate shaft, wherein the at least one proximal restraining member is also attached to the stent;
   at least one distal restraining member removably engaged with the inner elongate shaft, wherein the at least one distal restraining member is also attached to the stent;
   a proximal biasing member operatively engaged with at least a distal portion of the outer elongate shaft, the proximal biasing member configured to prevent unintentional disengagement of the at least one proximal restraining member from the outer elongate shaft;
   a distal biasing member operatively engaged with the at least one distal portion of the inner elongate shaft, the distal biasing member configured to prevent unintentional disengagement of the at least one distal restraining member from the inner elongate shaft; and
   an outer tube comprising a lumen extending at least partially therethrough, wherein the distal portion of the inner elongate shaft is at least partially movably disposed within the lumen of the outer tube, wherein the outer tube is disposed between the proximal biasing member and the distal biasing member;
   wherein movement of the inner elongate shaft relative to the outer elongate shaft in a first direction releases tension to the at least one proximal and distal restraining members to move the stent to the expanded configuration;
   wherein further movement of the inner elongate shaft relative to the outer elongate shaft in the first direction causes the outer tube to contact both the proximal and distal biasing members to release the at least one proximal restraining member from the outer elongate shaft and the at least one distal restraining member from the inner elongate shaft.

2. The stent delivery system of claim 1, further comprising:
   a proximal end stop fixedly attached to the distal portion of the outer elongate shaft;
   a distal end stop fixedly attached to the distal portion of the inner elongate shaft;
   a proximal pusher sleeve slidably disposed about the proximal portion of the inner elongate shaft and the distal portion of the outer elongate shaft and disposed between the proximal end stop and the outer tube; and
   a distal pusher sleeve slidably disposed about the distal portion of the inner elongate shaft and disposed between the distal end stop and the outer tube;
   wherein the distal biasing member is disposed between the distal end stop and the distal pusher sleeve and the proximal biasing member is disposed between the proximal end stop and the proximal pusher sleeve.

3. The stent delivery system of claim 2, wherein:
   the at least one proximal restraining member is removably engaged with the outer elongate shaft by a proximal hook fixedly attached to the outer elongate shaft; and
   the at least one distal restraining member is removably engaged with the inner elongate shaft by a distal hook fixedly attached to the inner elongate shaft, wherein the distal hook is attached to the inner elongate shaft at a point distal to the proximal hook.

4. The stent delivery system of claim 1, wherein:
   a proximal portion of the proximal biasing member is fixedly secured to the outer elongate shaft and a distal portion of the distal biasing member is fixedly secured to the inner elongate shaft.

5. The stent delivery system of claim 1, wherein:
   the at least one proximal restraining member is removably engaged with the outer elongate shaft by a proximal hook fixedly attached to the outer elongate shaft; and
   the at least one distal restraining member is removably engaged with the inner elongate shaft by a distal hook fixedly attached to the inner elongate shaft, wherein the distal hook is attached to the inner elongate shaft at a point distal to the proximal hook.

6. The stent delivery system of claim 1, wherein:
   the proximal biasing member comprises a proximal spring, wherein the proximal spring is slidably disposed about at least a portion of the outer elongate shaft; and
   the distal biasing member comprises a distal spring, wherein the distal spring is slidably disposed about the inner elongate shaft.

7. The stent delivery system of claim 1, wherein:
   movement of the inner and outer elongate shafts relative to each other in a second direction applies tension on the at least one proximal and distal restraining members to move the stent to the collapsed configuration.

8. The stent delivery system of claim 1, wherein:
   the stent delivery system further comprises a first position and a second position;
   wherein the inner elongate shaft is moved proximally with respect to the outer elongate shaft to move the stent delivery system from the first position to the second position;
   wherein the stent is in the expanded configuration in the second position and the stent is in the collapsed configuration in the first position.

9. The stent delivery system of claim 8, wherein:
   the stent delivery system further comprises a third position, wherein the inner elongate shaft is moved proximally with respect to the outer elongate shaft to move the stent delivery system from the second position to the third position;

wherein in the third position the at least one proximal restraining member is released from the outer elongate shaft and the at least one distal restraining member is released from the inner elongate shaft, thus releasing the stent from about the inner elongate shaft.

10. The stent delivery system of claim 9, wherein:

a proximal portion of the proximal biasing member is fixedly secured to the outer elongate shaft and a distal portion of the distal biasing member is fixedly secured to the inner elongate shaft;

wherein when the stent delivery system is moved from the second position to the third position the outer tube pushes a distal portion of the proximal biasing member in a proximal direction and a proximal portion of the distal biasing member in a distal direction.

11. The stent delivery system of claim 10, wherein:

the at least one proximal restraining member is removably engaged with the outer elongate shaft by a proximal hook fixedly attached to the outer elongate shaft; and the at least one distal restraining member is removably engaged with the inner elongate shaft by a distal hook fixedly attached to the inner elongate shaft, wherein the distal hook is attached to the inner elongate shaft at a point distal to the proximal hook;

wherein in the first and second position the at least one proximal restraining member is engaged with the proximal hook and the at least one distal restraining member is engaged with the distal hook;

wherein in the third position the at least one proximal restraining member is released from the proximal hook and the at least one distal restraining member is released from the distal hook.

12. The stent delivery system of claim 9, further comprising:

a proximal end stop fixedly attached to the distal portion of the outer elongate shaft;

a distal end stop fixedly attached to the distal portion of the inner elongate shaft;

a proximal pusher sleeve slidably disposed about the proximal portion of the inner elongate shaft and the distal portion of the outer elongate shaft and disposed between the proximal end stop and the outer tube; and a distal pusher sleeve slidably disposed about the distal portion of the inner elongate shaft and disposed between the distal end stop and the outer tube;

wherein the distal biasing member is disposed between the distal end stop and the distal pusher sleeve and the proximal biasing member is disposed between the proximal end stop and the proximal pusher sleeve;

wherein when the stent delivery system is moved from the second position to the third position the outer tube pushes the proximal pusher sleeve and the proximal biasing member in a proximal direction and the distal pusher sleeve and the distal biasing member in a distal direction.

13. The stent delivery system of claim 12, wherein:

the at least one proximal restraining member is removably engaged with the outer elongate shaft by a proximal hook fixedly attached to the outer elongate shaft; and the distal restraining member is removably engaged with the inner elongate shaft by a distal hook fixedly attached to the inner elongate shaft, wherein the distal hook is attached to the inner elongate shaft at a point distal to the proximal hook;

wherein in the first and second position the at least one proximal restraining member is engaged with the proximal hook and the at least one distal restraining member is engaged with the distal hook;

wherein in the third position the at least one proximal restraining member is released from the proximal hook and the at least one distal restraining member is released from the distal hook.

14. The stent delivery system of claim 13, wherein:

the proximal pusher sleeve comprises at least one prong, the at least one prong configured to engage with the proximal biasing member; and the distal pusher sleeve comprises at least one prong, the at least one prong configured to engage with the distal biasing member.

15. The stent delivery system of claim 1, further comprising:

a handle attached to a proximal portion of the outer elongate shaft and the proximal portion of the inner elongate shaft, wherein the handle is configured to control movement of the inner elongate shaft relative to the outer elongate shaft.

16. The stent delivery system of claim 15, further comprising:

a locking member attached to the handle having a locked configuration and a released configuration, wherein movement of the inner elongate shaft relative to the outer elongate shaft is restricted when the locking member is in the locked configuration.

17. A stent delivery system, comprising:

an inner elongate shaft comprising a proximal portion and a distal portion;

an outer elongate shaft comprising a lumen extending at least partially therethrough, wherein the proximal portion of the inner elongate shaft is at least partially movably disposed within the lumen;

a stent positionable about the inner elongate shaft, the stent having a collapsed configuration and an expanded configuration;

at least one proximal restraining member removably engaged with the outer elongate shaft, wherein the at least one proximal restraining member is also attached to the stent;

at least one distal restraining member removably engaged with the inner elongate shaft, wherein the at least one distal restraining member is also attached to the stent;

a proximal biasing member operatively engaged with at least a distal portion of the outer elongate shaft, the proximal biasing member configured to prevent unintentional disengagement of the at least one proximal restraining member from the outer elongate shaft;

a distal biasing member operatively engaged with the distal portion of the inner elongate shaft, the distal biasing member configured to prevent unintentional disengagement of the at least one distal restraining member from the inner elongate shaft;

an outer tube comprising a lumen extending at least partially therethrough, wherein the distal portion of the inner elongate shaft is at least partially movably disposed within the lumen of the outer tube, wherein the outer tube is disposed between the proximal biasing member and the distal biasing member;

a proximal end stop fixedly attached to the distal portion of the outer elongate shaft;

a distal end stop fixedly attached to the distal portion of the inner elongate shaft;

a proximal pusher sleeve slidably disposed about the proximal portion of the inner elongate shaft and the distal portion of the outer elongate shaft and disposed between the proximal end stop and the outer tube; and a distal pusher sleeve slidably disposed about the distal portion of the inner elongate shaft and disposed between the distal end stop and the outer tube;

wherein the distal biasing member is disposed between the distal end stop and the distal pusher sleeve and the proximal biasing member is disposed between the proximal end stop and the proximal pusher sleeve;

wherein movement of the inner elongate shaft relative to the outer elongate shaft in a first direction releases tension to the at least one proximal and distal restraining members to move the stent to the expanded configuration.

18. A method for delivering a stent, comprising:

inserting a distal portion of a stent delivery system into a body lumen of a patient, the stent delivery system comprising:

an inner elongate shaft comprising a proximal portion and a distal portion;

an outer elongate shaft comprising a lumen extending at least partially therethrough, wherein the proximal portion of the inner elongate shaft is at least partially movably disposed within the lumen;

a stent positionable about the inner elongate shaft, the stent having a collapsed configuration and an expanded configuration;

at least one proximal restraining member removably engaged with the outer elongate shaft, wherein the at least one proximal restraining member is also attached to the stent;

at least one distal restraining member removably engaged with the inner elongate shaft, wherein the at least one distal restraining member is also attached to the stent;

a proximal biasing member operatively engaged with at least a distal portion of the outer elongate shaft, the proximal biasing member configured to prevent unintentional disengagement of the at least one proximal restraining member from the outer elongate shaft;

a distal biasing member operatively engaged with the distal portion of the inner elongate shaft, the distal biasing member configured to prevent unintentional disengagement of the at least one distal restraining member from the inner elongate shaft; and an outer tube comprising a lumen extending at least partially therethrough, wherein the distal portion of the inner elongate shaft is at least partially movably disposed within the lumen of the outer tube, wherein the outer tube is disposed between the proximal biasing member and the distal biasing member;

maintaining the stent in the collapsed configuration with the inner and outer elongate shafts in a first position and tension applied to the at least one proximal and at least one distal restraining members for delivery of the stent to an implant site;

positioning the stent at the implant site;

expanding the stent to the expanded configuration by moving the inner and outer elongate shafts relative to each other to a second position, thereby releasing tension on the at least one proximal and distal restraining members so that the stent moves to the expanded configuration; and releasing the stent from about the inner and outer elongate shafts by moving the inner and outer elongate shafts relative to each other to a third position, thereby causing the outer tube to contact both the proximal and distal biasing members to release the at least one proximal restraining member from the outer elongate shaft and the at least one distal restraining member from the inner elongate shaft.

19. The method of claim 18, further comprising:

returning the inner and outer elongate shafts to the first position to move the stent from the expanded configuration to the collapsed configuration.

20. The method of claim 18, wherein:

the stent delivery system further comprises:

a proximal end stop fixedly attached to the distal portion of the outer elongate shaft;

a distal end stop fixedly attached to the distal portion of the inner elongate shaft;

a proximal pusher sleeve slidably disposed about the proximal portion of the inner elongate shaft and the distal portion of the outer elongate shaft and disposed between the proximal end stop and the outer tube; and a distal pusher sleeve slidably disposed about the distal portion of the inner elongate shaft and disposed between the distal end stop and the outer tube;

wherein the distal biasing member is disposed between the distal end stop and the distal pusher sleeve and the proximal biasing member is disposed between the proximal end stop and the proximal pusher sleeve.

* * * * *

UNITED STATES PATENT AND TRADEMARK OFFICE
CERTIFICATE OF CORRECTION

PATENT NO. : 9,889,027 B2  
APPLICATION NO. : 14/836405  
DATED : February 13, 2018  
INVENTOR(S) : Triona Campbell et al.

Page 1 of 1

It is certified that error appears in the above-identified patent and that said Letters Patent is hereby corrected as shown below:

In the Claims

In Column 11, Claim 1, Lines 47-48, after "engaged with the", delete "at least one".

Signed and Sealed this  
Eighteenth Day of June, 2019

Andrei Iancu  
*Director of the United States Patent and Trademark Office*